United States Patent
Häfner

(10) Patent No.: US 6,858,223 B2
(45) Date of Patent: Feb. 22, 2005

(54) COMPOSITIONS COMPRISING PHENYLAMINOTHIOPHENACETIC ACID DERIVATIVES FOR THE TREATMENT OF ACUTE OR ADULT RESPIRATORY DISTRESS SYNDROME (ARDS) AND INFANT RESPIRATORY DISTRESS SYNDROME (IRDS)

(75) Inventor: Dietrich Häfner, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/160,100

(22) Filed: Jun. 4, 2002

(65) Prior Publication Data

US 2003/0007931 A1 Jan. 9, 2003

Related U.S. Application Data

(63) Continuation of application No. 09/701,574, filed as application No. PCT/EP99/04276 on Jun. 19, 1999, now abandoned.

(30) Foreign Application Priority Data

Jun. 23, 1998 (DE) .......................................... 198 27 907

(51) Int. Cl.$^7$ .......................... A61F 13/00; A61K 9/127; A61K 35/42; A01N 43/06
(52) U.S. Cl. ........................ 424/434; 424/450; 424/557; 424/489; 514/447; 549/68
(58) Field of Search ............................... 424/422, 450, 424/43, 46, 557, 400, 455; 514/447, 951; 549/68

(56) References Cited

U.S. PATENT DOCUMENTS

| | | | |
|---|---|---|---|
| 4,272,507 A | * | 6/1981 | Figala .......................... 514/447 |
| 4,571,334 A | * | 2/1986 | Yoshida et al. .............. 424/557 |
| 4,944,941 A | * | 7/1990 | Ammann .................... 424/85.5 |
| 5,006,343 A | | 4/1991 | Benson et al. ............... 424/450 |
| 5,049,389 A | * | 9/1991 | Radhakrishnan ............ 424/450 |
| 5,891,844 A | | 4/1999 | Häfner ........................... 514/7 |

FOREIGN PATENT DOCUMENTS

| | | |
|---|---|---|
| EP | 0 005 559 | 11/1979 |
| EP | 0 055 041 | 6/1982 |
| WO | 83/02672 | 8/1983 |
| WO | 96/09831 | 4/1996 |

OTHER PUBLICATIONS

Bernard et al.; The Effects of Ibuprofen on the Physiology and Survival of Patients with Sepsis; The New England Journal of Medicine; Vol. 336, No. 13, (1997), pp. 912–918.

Leeman; The Pulmonary Circulation in Acute Lung Injury: A Review of Some Recent Advances; Intensive Care Medicine; 17, (1991), pp. 254–260.

* cited by examiner

Primary Examiner—Thurman K. Page
Assistant Examiner—Sharmila S Gollamudi
(74) Attorney, Agent, or Firm—Jacobson Holman PLLC

(57) ABSTRACT

A composition comprising a combination of a compound of formula I

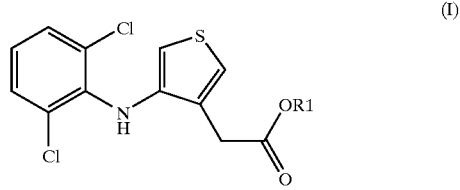

(I)

in which R1 is hydrogen or 2-(2-hydroxyethoxy)ethyl and/or a pharmacologically tolerable salt thereof, and lung surfactant is useful for treating patients afflicted with IRDS or ARDS.

17 Claims, No Drawings

COMPOSITIONS COMPRISING PHENYLAMINOTHIOPHENACETIC ACID DERIVATIVES FOR THE TREATMENT OF ACUTE OR ADULT RESPIRATORY DISTRESS SYNDROME (ARDS) AND INFANT RESPIRATORY DISTRESS SYNDROME (IRDS)

This is a continuation of application Ser. No. 09/701,574 filed Dec. 8, 2000 now abandoned, which in turn is a 371 of PCT/EP99/04276 filed Jun. 19, 1999.

TECHNICAL FIELD

The invention relates to a novel composition for the treatment of disease conditions which are designated as infant Respiratory Distress Syndrome (IRDS) and Acute or Adult Respiratory Distress Syndrome (ARDS).

PRIOR ART

Adult Respiratory Distress Syndrome (ARDS) is a descriptive expression which is applied to a large number of acute, diffusely infiltrative pulmonary lesions of different etiology if they are associated with a severe gas exchange disorder (in particular arterial hypoxemia). The expression ARDS is used because of the numerous common clinical and pathological features with the Infant Respiratory Distress Syndrome (IRDS). If, in the case of IRDS, the lung surfactant deficiency caused by premature birth is predominant, then in the case of ARDS a lung surfactant malfunction is caused by a lung disorder based on differing etiologies.

Triggering causes for ARDS can, for example, be (cited in accordance with Harrison's Principles of Internal Medicine 10th Ed. 1983 McGraw-Hill Int. Book Comp.) diffuse pulmonary infections (for example due to viruses, bacteria, fungi), aspiration of, for example, gastric juice or in the case of near-drowning, inhalation of toxins or irritants (for example chlorine gas, nitrogen oxides, smoke), direct or indirect trauma (for example multiple fractures or pulmonary contusion), systemic reactions to inflammations outside the lung (for example hemorrhagic pancreatitis, gram-negative septicemia), transfusions of high blood volumes or alternatively after cardiopulmonary bypass.

With a mortality of 50–60% (survey in Schuster Chest 1995, 107:1721–26), the prognoses of an ARDS patient are still to be designated as very unfavorable.

The therapy of ARDS consists mainly in the earliest possible application of different forms of ventilation [for example PEEP (positive end-expiratory pressure), raising of the oxygen concentration of the respiratory air, SIMV (Synchronized Intermittent Mandatory Ventilation; Harrison's Principles of Internal Medicine 10th Ed. 1983 McGraw-Hill Int. Book Comp.)] up to extracorporeal membrane oxygenation (ECMO; Zapol and Lemaire Adult Respiratory Distress Syndrome, Marcel Dekker Inc, 1991).

The targetted use of various ventilation techniques has only led to a small lowering of mortality and includes the risk of setting in motion a vicious circle. By ventilation with pressure and high $FiO_2$ (Fraction of Inspired Oxygen; proportion of oxygen in the respiratory air), the lungs themselves can be damaged and as a result of this even higher pressures and higher $FiO_2$ may be required in order to obtain an adequate oxygenation of the blood.

Different approaches to the solution of the abovementioned problems are followed. These include lung surfactant substitution [survey, for example, B. Lachmann, D. Gommers and E. P. Eijking: Exogenous surfactant therapy in adults, Atemw.-Lungenkrkh. 1993, 19:581–91; T. J. Gregory et al: Bovine Surfactant Therapy for Patients with Acute Respiratory Distress Syndrome, Am. J. Respir. Crit. Care Med. 1997, Vol. 155, 1309–1315] up to purely antiinflammatory therapy with, for example, prostaglandin $E_1$ ($PGE_1$; Abraham et al. Crit Care Med 1996, 24:10–15) or glucocorticosteroids (Bernard et al. N Engl J Med 1987, 317:1565–70). Although certain successes were achieved by the administration of lung surfactant (for example Walmrath et al. Am J Resp Crit Care Med 1996, 154:57–62), the purely antiinflammatory therapies hitherto led to little if any success. There is a certain contrast here to the pathological or histopathological findings in ARDS. Thus, massive polymorphonuclear leucocyte infiltrations (survey, for example, Thiel et al. Anaesthesist 1996, 45:113–130) were found in the lungs and the lavage of patients with ARDS, and a number of inflammatory mediators are detectable. Still under investigation were $PGE_1$ in a liposomal intravenous administration form (Abraham et al. Crit Care Med 1996, 24:10–15) and substances which aim at the inhibition of phosphatidic acids (for example lisofylline; Rice et al. Proc Natl Acad Sci 1994, 91:3857–61) or recombinant human interleukin 1 (IL-1) receptor antagonists (Fisher et al. JAMA 1994, 271:1836–43). Both $PGE_1$ and the IL-1 receptor antagonist, however are restricted in their therapeutic utility due to side effects, and the clinical studies were terminated or concluded without success.

WO96/09831 indicates compositions for the treatment of ARDS and IRDS which contain a glucocorticosteroid and lung surfactant.

EP-B-0 451 215 describes compositions for the administration of a pharmaceutically active compound via the lungs. These compositions include liposomes which contain a pharmaceutically active compound and a lung surfactant protein. These systems are likewise proposed for the treatment of ARDS and IRDS. EP-B-0 055 041 describes preparations for inhalation or infusion for the treatment of disorders of the respiratory organs, which contain an active compound against disorders of the respiratory organs and natural lung surfactant. Preparations for the treatment of ARDS or IRDS are not disclosed.

DESCRIPTION OF THE INVENTION

It has now surprisingly been found that by the administration of a combination of a compound of the formula I

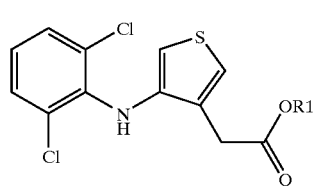

(I)

in which R1 is hydrogen or 2-(2-hydroxyethoxy)ethyl and lung surfactant a synergistic effect can be achieved in the treatment of IRDS and ARDS.

The invention therefore provides a composition for the treatment of IRDS or ARDS comprising a compound of the formula I in which R1 is as defined above and/or a pharmacologically tolerable salt of this compound and lung surfactant.

Further embodiments of the invention follow from the patent claims.

The preparation of compounds of the formula I and their use as antiinflammatory agents is described in EP-B1-0 005 559.

Suitable pharmacologically tolerable salts of the compounds of the formula I are, in particular if R1 is hydrogen, the salts with bases. Examples which may be mentioned are the alkali metal (lithium, sodium, potassium) or the calcium, aluminium, magnesium, titanium, ammonium, meglumine or guanidinium salts, where the bases are employed in the salt preparation in an equimolar ratio or in a ratio which differs therefrom—depending on whether it is a mono- or polybasic base and on which salt is desired.

Natural lung surfactant has surface-active properties; for example, it reduces the surface tension in the pulmonary alveolae. A simple and fast in vitro test for the determination of the surface activity of lung surfactant is, for example, the so-called Wilhelmy balance [Goerke, J Biochim Biophys Acta, 344: 241–261 (1974), King R. J. and Clements J. A., Am J Physiol 223: 715–726 (1972)]. This method gives indications about the quality of the lung surfactant, measured as the action of a lung surfactant to achieve a surface tension of almost zero mN/m.

In the test with the Wilhelmy balance, a suspension of lung surfactant having a defined phospholipid concentration is injected into an aqueous solution. The phospholipids are distributed at the gas/liquid phase boundary, forming a so-called monolayer. This monolayer reduces the surface tension of the water. A small platinum sheet is carefully immersed in the solution. The force which pulls the platinum sheet down can now be determined using sensitive transformers. This force is proportional to the surface tension and depends on the size of the platinum sheet. Another measuring device for determining the surface activity of lung surfactant is the "Pulsating Bubble Surfactometer" (Possmayer F., Yu S. and Weber M., Prog Resp Res, Ed. v. Wichert, Vol. 18: 112–120 (1984)].

The activity of a lung surfactant composition can also be determined by in vivo tests, for example as described in the subsequent "pharmacology" section. Indications about the activity of a lung surfactant can be obtained by measuring, for example, lung compliance, blood gas exchange or the required respiratory pressures.

Lung surfactant is understood according to the invention as meaning the numerous known compositions and their modifications which have the function of natural lung surfactant. Preference is given here to those compositions which are active, for example, in the tests described above. Particular preference is given to those compositions which, in comparison to natural, in particular human, lung surfactant, show increased activity in such a test. These can be compositions which contain only phospholipids, but also compositions which, in addition to the phospholipids, contain lung surfactant protein, inter alia. Commercially available products which may be mentioned are Curosurf® (Serono, Pharma GmbH, Unterschleigßheim), a highly purified natural surfactant from homogenized pigs' lungs, Survanta® (Abbott GmbH, Wiesbaden) and Alveofact® (Dr. Karl Thomae GmbH Biberach), both extracts of bovine lungs, and also Exosurf® (Deutsche Wellcome GmbH, Burgwedel), a synthetic phospholipid with auxiliaries. Possible lung surfactant proteins are both the proteins obtained from natural sources, such as, for example, pulmonary lavage or extraction from amniotic fluid, and also the gentically engineered proteins. According to the invention, the lung surfactant proteins designated by SP-B and SP-C and their modified derivatives are particularly of interest. The amino acid sequences of these lung surfactant proteins, their isolation or preparation by genetic engineering are known (for example from WO86/03408, EP-A-0 251 449, WO89/04326, WO87/06943, WO88/03170, WO91/00871, EP-A-0 368 823 and EP-A-0 348 967). Modified derivatives of the lung surfactant proteins designated by SP-C, which differ from human SP-C in that some amino acids have been exchanged, are described, for example, in WO91/18015 and WO95/32992. In this context, the recombinant SP-C derivatives disclosed in WO95/32992 are to be particularly emphasized, in particular those which differ from human SP-C in positions 4 and 5 by the exchange of cysteine for phenylalanine and in position 32 by the exchange of methionine for isoleucine [hereinbelow designated rSP-C (FF/I)]. EP-B-0 100 910, EP-A-0 110 498, EP-B-0 119 056, EP-B-0 145 005 and EP-B-0 286 011 describe phospholipid compositions with or without lung surfactant proteins which are likewise suitable as components of the preparations according to the invention.

The invention furthermore provides the use of the compositions according to the invention for the production of medicaments which are employed for the treatment and/or prophylaxis of IRDS or ARDS.

Moreover, the invention provides medicaments for the treatment and/or prophylaxis of the abovementioned diseases, which comprise a composition according to the invention.

The compositions according to the invention are made available either in liquid form for intratracheal or intrabronchial administration or in powder form for administration by inhalation. The compositions are prepared by procedures familiar to those skilled in the art, if appropriate using further suitable pharmaceutical auxiliaries. A powder form is obtained, for example, by mixing liquid lung surfactant preparations, for example aqueous suspensions, with aqueous suspensions of 4-(2,6-dichloroanilino)-3-thiopheneacetic acid or 2-(2-hydroxyethoxy)ethyl 4-(2,6-dichloroanilino)-3-thiopheneacetate and then lyophilizing and micronizing it. Alternatively, a solution of a lung surfactant and 4-(2,6-dichloroanilino)-3-thiopheneacetic acid or 2-(2-hydroxyethoxy)ethyl 4-(2,6-dichloroanilino)-3-thiopheneacetate can be lyophilized in a suitable solvent, such as, for example, tert-butanol, and then micronized. Spray-drying of a mixture of an aqueous lung surfactant suspension and an aqueous 4-(2,6-dichloroanilino)-3-thiopheneacetic acid suspension or a 2-(2-hydroxyethoxy) ethyl 4-(2,6-dichloroanilino)-3-thiopheneacetate suspension or a solution of a lung surfactant and 4-(2,6-dichloroanilino)-3-thiopheneacetic acid or 2-(2-hydroxyethoxy)ethyl 4-(2,6-dichloroanilino)-3-thiopheneacetate in suitable solvents, such alcohols (for example methanol, ethanol, 2-propanol), chloroform, dichloromethane, acetone and their mixtures, which optionally can additionally contain small amounts of water, also leads to powdered preparations. Administration by inhalation can also be carried out by atomizing solutions or suspensions which contain the compositions according to the invention. Compositions according to the invention advantageously contain 1 to 30 percent by weight of 4-(2, 6-dichloroanilino)-3-thiopheneacetic acid or 2-(2-hydroxyethoxy)ethyl 4-(2,6-dichloroanilino)-3-thiopheneacetate.

Below, the preparation of a powdered preparation by spray-drying is described by way of example:

EXAMPLE 1

5.46 g of 1,2-dipalmitoyl-3-sn-phosphatidylcholine, 2.31 g of 1-palmitoyl-2-oleoyl-3-sn-phosphatidylglycerolammonium, 0.9 g of 4-(2,6-dichloroanilino)-3-thiopheneacetic acid, 0.38 g of palmitic acid, 0.21 g of calcium chloride and 0.15 g of rSP-C [recombinant lung surfactant protein SP-C (FF/I)] are dissolved in 500 ml of 2-propanol/water (90:10) and spray-dried in a laboratory spray drier Büchi B 191. Spray conditions: the gas for drying is nitrogen, the inlet temperature is 110° C., the outlet temperature is 58–62° C. This gives a fine white powder.

EXAMPLE 2

5.46 g of 1,2-dipalmitoyl-3-sn-phosphatidylcholine, 2.31 g of 1-palmitoyl-2-oleoyl-3-sn-phosphatidylglycerolammonium, 0.09 g of 4-(2,6-dichloroanilino)-3- thiopheneacetic acid, 0.38 g of palmitic acid, 0.21 g of calcium chloride and 0.15 g of rSP-C [recombinant lung surfactant protein SP-C (FF/I)] are dissolved in 500 ml of 2-propanol/water (90:10) and spray-dried in a laboratory spray drier Büchi B 191. Spray conditions: the gas for drying is nitrogen, the inlet temperature is 110° C., the outlet temperature is 58–62° C. This gives a fine white powder.

The invention also provides a method for treating mammals, including humans, suffering from IRDS or ARDS. The method comprises administering a therapeutically effective and pharmacologically tolerable amount of one of the compositions according to the invention to the diseased mammal.

The invention furthermore provides the compositions according to the invention for use in the treatment of IRDS and ARDS.

The preparations according to the invention are administered, for example, 3 to 4 times daily for 2 to 4 days. For example, preparations comprising 6 mg of 4-(2,6-dichloroanilino)-3-thiopheneacetic acid and 50 mg of phospholipids are administered 6 times at an interval of 6 hours by inhalation or intratracheally or intrabronchially.

Pharmacology

Anesthetized Sprague Dawley rats are artificially ventilated with pure oxygen and a positive end-exiratory pressure (PEEP; in order to ensure oxygenation of the rats) and lavaged until their endogenous lung surfactant is washed out [D. Häfner, R. Beume, U. Kilian, G. Kraznai and Burkhard Lachmann: Dose-response comparison of five lung surfactant (LSF) preparations in an animal model of adult respiratory distress syndrome (ARDS); D. Häfner, P.-G. Germann, D. Hauschke, Pulmonary Pharmacology (1994) 7, 319–332]. This is manifested by the fact that in the animals the preliminary values of the arterial oxygen partial pressure ($PaO_2$) of 500–550 mmHg (in the case of pure oxygen ventilation and PEEP) decrease to values of 50–110 mmHg.

Animals of the control group which are not treated with lung surfactant remain with their $PaO_2$ at these low values throughout the observation period. 60 minutes after the $PaO_2$ has decreased to these values, lung surfactant or lung surfactant together with 4-(2,6-dichloroanilino)-3-thiopheneacetic acid is instilled intratracheally. The blood gases are determined 30, 60, 90 and 120 minutes after instillation.

In Table 1 below, in line A the average values (±standard deviation) of the $PaO_2$ are indicated in mmHg for the time 120 minutes (constant PEEP of 8 cm $H_2O$) after intratracheal instillation of lung surfactant 1 h after the last lavage. The table contains data about the values after a sole i.v. administration of 4-(2,6-dichloroanilino)-3-thiopheneacetic acid (Eltenac) in comparison to untreated controls. It can be seen from the table that the sole administration of Eltenac has no influence on the $PaO_2$. This follows by comparison with the untreated control animals. The administration of lung surfactant (25 or 100 mg/kg) leads to a rise in the $PaO_2$. The i.v. administration of 4-(2,6-dichloroanilino)-3-thiopheneacetic acid (Eltenac) together with the low dose (25 mg/kg) of lung surfactant results in a significant dose-dependent improvement of the $PaO_2$ values to the level of a 100 mg/kg dose of lung surfactant. In Table 2, in line A the $PaO_2$ values after joint intratracheal (i.tr.) administration of lung surfactant together with Eltenac are indicated in increasing dosages. The addition of 0.1 to 0.3 mg/kg of Eltenac to the dose of 25 mg/kg of lung surfactant improves the $PaO_2$ values in comparison with the lung surfactant dose of 25 mg/kg. It follows from this that the joint administration of Eltenac and lung surfactant leads to an unexpected superadditive effect. It is therefore possible to save a part of the very expensive lung surfactant, or else to obtain an increased effect of each individual component. Moreover, the comparison of the effects of Eltenac after i.v. and i.tr. administration shows that, after joint i.tr. administration with lung surfactant, the required amount of Eltenac is significantly lower than after i.v. administration.

TABLE 1

$PaO_2$ values for the time 120 min after intratracheal (i.tr.) administration of lung surfactant 1 h after the last lavage and i,tr. administration of lung surfactant plus intravenous (i.v.) administration of Eltenac directly after lavage in comparison with untreated controls and controls which received only i.v. Eltenac after the last lavage.

| | Control | Eltenac i.v. | Lung surfactant i.tr. | | Lung surfactant i.tr. 25 mg/kg + Eltenac i.v. | | |
|---|---|---|---|---|---|---|---|
| | | 22.1 mg/kg | 25 mg/kg | 100 mg/kg | 2.2 mg/kg | 6.6 mg/kg | 22.1 mg/kg |
| A | 54 ± 6 | 82 ± 35 | 262 ± 128 | 457 ± 58 | 328 ± 118 | 391 ± 97 | 410 ± 110 |

TABLE 2

$PaO_2$ values for the time 120 min after joint intratracheal (i.tr.) administration of lung surfactant and Eltenac 1 h after the last lavage in comparison with untreated controls and controls which received only i.tr. Eltenac after the last lavage.

| | Control | Eltenac i.tr. | Lung surfactant i.tr. | | Lung surfactant i.tr. 25 mg/kg + Eltenac i.tr | | |
|---|---|---|---|---|---|---|---|
| | | 3.0 mg/kg | 25 mg/kg | 100 mg/kg | 0.1 mg/kg | 0.3 mg/kg | 1.0 mg/kg |
| A | 72 ± 42 | 92 ± 69 | 352 ± 117 | 480 ± 53 | 409 ± 102 | 493 ± 54 | 402 ± 52 |

The histological work-ups of the lungs of these animals carried out after the experiment show a strong formation of so-called hyaline membranes (HM) and a strong influx of inflammatory cells [for example polymorphonuclear neutrophilic leucocytes (PMNL)] as an expression of the development of Acute Respiratory Distress Syndrome. The effects seen for the $PaO_2$ values are likewise confirmed in the histological studies.

In the investigation of preparations according to the invention comprising Eltenac and lung surfactant (phospholipid mixture) with or without surfactant proteins in this model, it was found that the oxygenation and the histological changes (inhibition of the formation of HM and inhibition of the influx of PMNL) improve superadditively in comparison with the sole administration of lung surfactant or Eltenac. It follows that as a result of this unexpected synergistic effect the treatment of IRDS and ARDS can be shortened and the high mortality accompanying these syndromes can be reduced.

What is claimed is:

1. A composition for the treatment of IRDS and ARDS comprising
   a) a compound of formula I

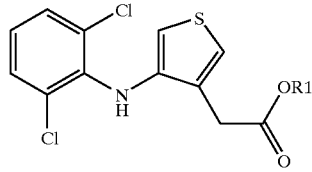

in which R1 is hydrogen or 2-(2-hydroxyethoxy)ethyl and/or a pharmacologically tolerable salt of this compound and b) a phospholipid comprising lung surfactant.

2. A composition for the treatment of IRDS and ARDS comprising 4-(2,6-dichloroanilino)-3-thio-phene-acetic acid and/or one of its pharmacologically tolerable salts and a phospholipid comprising lung surfactant.

3. A composition as claimed in claim 1, wherein the lung surfactant comprises a mixture of phospholipids.

4. A composition as claimed in claim 3, wherein the phospholipids are those which occur in natural lung surfactant.

5. A composition as claimed in claim 3, which further comprises lung surfactant protein.

6. A composition as claimed in claim 5, wherein the lung surfactant protein is a member selected from the group consisting of SP-B, SP-C and a modified derivative of either.

7. A composition as claimed in claim 1, wherein the lung surfactant is that obtained by pulmonary lavage.

8. A composition as claimed in claim 2, wherein the lung surfactant comprises a mixture of phospholipids.

9. A composition as claimed in claim 8, wherein the phospholipids are those which occur in natural lung surfactant.

10. A composition as claimed in claim 4, which further comprises lung surfactant protein.

11. A composition as claimed in claim 10, wherein the lung surfactant protein is a member selected from the group consisting of SP-B, SP-C and a modified derivative of either.

12. A method of compounding a pharmaceutical composition for controlling IRDS and ARDS which comprises combining a phospholipid comprising lung surfactant with a compound of formula I,

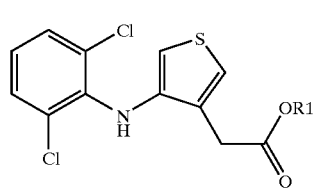

in which R1 is hydrogen or 2-(2-hydroxyethoxy)ethyl, or a pharmacologically tolerable salt thereof.

13. A method of treating a patient afflicted with IRDS or ARDS, which comprises administering to the patient an effective amount of a composition as claimed in claim 1.

14. A method of treating a patient afflicted with IRDS or ARDS, which comprises administering to the patient an effective amount of a composition as claimed in claim 2.

15. A method of claim 12, which comprises spray drying a) an admixture of an aqueous suspension of a phospholipid comprising lung surfactant and an aqueous suspension of 4-(2,6-dichloroanilino)-3-thiophene-acetic acid or b) a solution of a phospholipid comprising lung surfactant and the 4-(2,6-dichloroanilino)-3-thiophene-acetic acid in a suitable solvent, wherein the 4-(2,6-dichlooanilino)-3-thiophene-acetic acid is optionally in the form of a pharmaceuticlaly tolerable salt thereof, to obtain the composition in powder from.

16. A method of elevating the arterial oxygen partial pressure in patients afflicted with IRDS or ARDS, which comprises administering to the patient an effective amount of a composition as claimed in claim 1.

17. A method to inhibit (or minimize) the formation of hyaline membranes in the lungs of patients afflicted with IRDS or ARDS, which comprises administering to the patient an effective amount of a composition as claimed in claim 1.

* * * * *